United States Patent
Suh et al.

(10) Patent No.: US 10,582,954 B2
(45) Date of Patent: *Mar. 10, 2020

(54) CLIVUS PLATE

(71) Applicant: GLOBUS MEDICAL, INC., Audubon, PA (US)

(72) Inventors: Sean Suh, Morganville, NJ (US); Roy T. Daniel, Epalinges (CH)

(73) Assignee: Globus Medical, Inc., Audubon, PA (US)

(*) Notice: Subject to any disclaimer, the term of this patent is extended or adjusted under 35 U.S.C. 154(b) by 177 days.

This patent is subject to a terminal disclaimer.

(21) Appl. No.: 15/426,590

(22) Filed: Feb. 7, 2017

(65) Prior Publication Data

US 2017/0143380 A1 May 25, 2017

Related U.S. Application Data

(63) Continuation of application No. 14/661,154, filed on Mar. 18, 2015, now Pat. No. 9,597,123, which is a continuation of application No. 12/511,733, filed on Jul. 29, 2009, now Pat. No. 9,011,500.

(51) Int. Cl.
*A61B 17/70* (2006.01)
*A61B 17/80* (2006.01)
*A61F 2/44* (2006.01)

(52) U.S. Cl.
CPC ...... *A61B 17/7055* (2013.01); *A61B 17/7059* (2013.01); *A61B 17/8033* (2013.01); *A61F 2/44* (2013.01); *A61F 2/4455* (2013.01)

(58) Field of Classification Search
CPC .................. A61B 17/7055; A61B 17/7059
See application file for complete search history.

(56) References Cited

U.S. PATENT DOCUMENTS

| | | | | |
|---|---|---|---|---|
| 5,127,912 A * | 7/1992 | Ray | ........... | A61B 17/7041 606/250 |
| 5,167,664 A * | 12/1992 | Hodorek | ........... | A61B 17/8685 606/306 |
| 6,001,130 A * | 12/1999 | Bryan | ........... | A61B 17/686 606/247 |
| 6,328,738 B1 * | 12/2001 | Suddaby | ........... | A61B 17/1757 606/282 |
| 6,355,036 B1 * | 3/2002 | Nakajima | ........... | A61B 17/66 606/54 |
| 6,902,565 B2 * | 6/2005 | Berger | ........... | A61B 17/7055 606/250 |
| 2005/0171544 A1 * | 8/2005 | Falkner, Jr. | ........... | A61B 17/1728 606/281 |
| 2006/0004363 A1 * | 1/2006 | Brockmeyer | ........... | A61B 17/7055 606/281 |
| 2006/0089648 A1 * | 4/2006 | Masini | ........... | A61B 17/1615 606/71 |
| 2006/0111782 A1 * | 5/2006 | Petersen | ........... | A61B 17/1604 623/17.11 |
| 2007/0118129 A1 * | 5/2007 | Fraser | ........... | A61F 2/0811 606/71 |

(Continued)

*Primary Examiner* — Zade Coley

(57) ABSTRACT

The present disclosure generally relates to a fixation device for positioning and immobilizing at least two adjacent vertebrae. In particular, in one or more embodiments, the present disclosure relates to an anterior clivus plate that immobilizes at least two adjacent vertebrae.

18 Claims, 3 Drawing Sheets

(56) References Cited

U.S. PATENT DOCUMENTS

| | | | |
|---|---|---|---|
| 2007/0123989 A1* | 5/2007 | Gfeller | A61B 17/562 623/17.16 |
| 2008/0177263 A1* | 7/2008 | Freedman | A61B 17/7059 606/71 |
| 2009/0036894 A1* | 2/2009 | Henderson, Sr. | A61B 17/7055 606/60 |
| 2009/0210062 A1* | 8/2009 | Thalgott | A61F 2/4465 623/17.16 |
| 2009/0287258 A1* | 11/2009 | Vannemreddy | A61B 17/7059 606/298 |

* cited by examiner

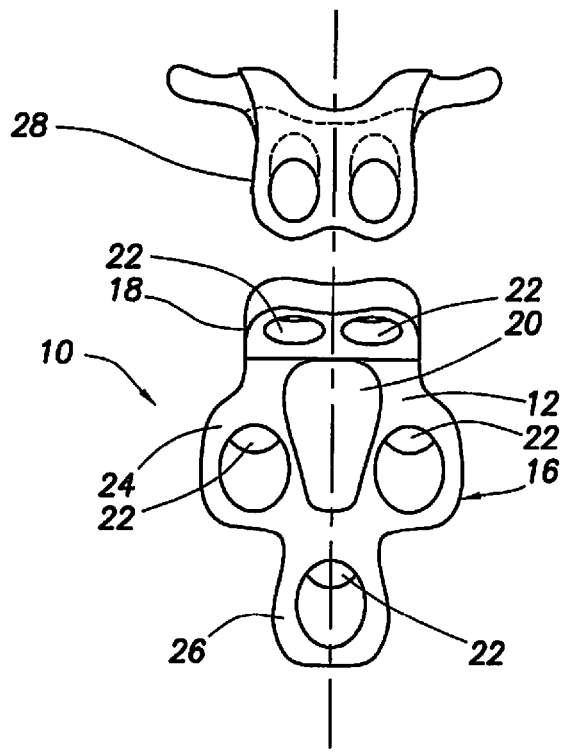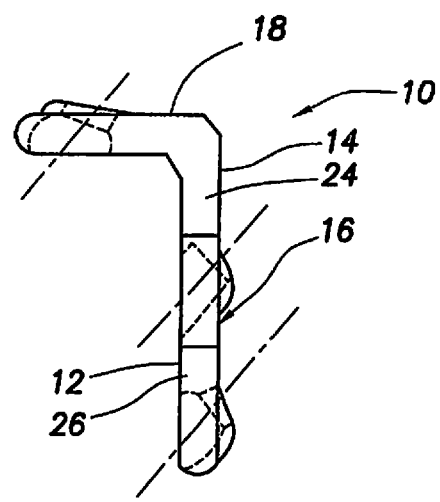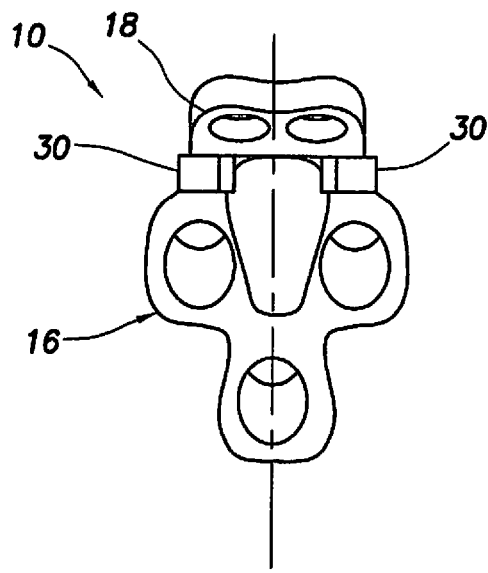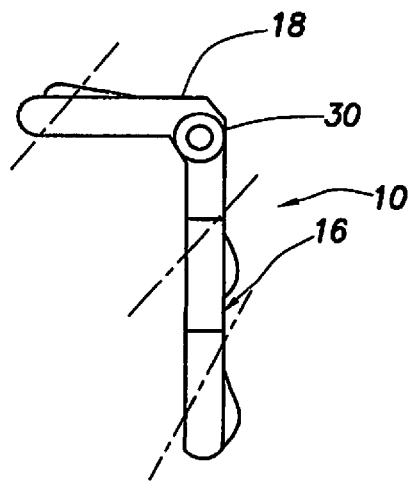
FIG. 1
FIG. 2
FIG. 3
FIG. 4

CLIVUS PLATE

CROSS REFERENCE TO RELATED APPLICATIONS

The present application is a continuation of U.S. Ser. No. 14/661,154, filed Mar. 18, 2015, which is a continuation application of U.S. Ser. No. 12/511,733, filed Jul. 29, 2009, now issued as U.S. Pat. No. 9,011,500, the entire contents of which are incorporated by reference in their entireties.

FIELD OF THE INVENTION

The present disclosure generally relates to a fixation device for positioning and immobilizing at least two adjacent vertebrae. In particular, in one or more embodiments, the present disclosure relates to an anterior clivus plate that immobilizes at least two adjacent vertebrae.

BACKGROUND OF THE INVENTION

Bones and bony structures are susceptible to a variety of weaknesses that can affect their ability to provide support and structure. Weaknesses in bony structures may have many causes, including degenerative diseases, tumors, fractures, and dislocations. By way of example, rheumatoid arthritis may lead to weakness in the C1-C2 articulation, resulting, for example, in basilar invagination. Advances in medicine and engineering have provided doctors with a plurality of devices and techniques for alleviating or curing these weaknesses.

Typically, weaknesses in the spine are corrected by using devises that fuse one or more vertebrae together. Common devices involve plate systems that align and maintain adjacent cervical vertebrae in a desired position, with desired spacing. These devices, commonly referred to as bone fixation plating systems, typically include one or more plates and screws for aligning and holding vertebrae in a fixed position with respect to one another. In the treatment of basilar invagination, devices that fix one or more adjacent vertebrae may be used either alone or in combination with decompression. By way of example, occipitocervical fusion may be used for a rheumatoid arthritis patient with basilar invagination.

Thus, there is a need for a plate system that provides structural stability to adjacent vertebrae, for example, a plate system that provides structural stability to the C1-C2 articulation.

SUMMARY OF THE INVENTION

An embodiment of the present invention provides an implantable device. The implantable device may comprise a bone plate having a lower surface configured to contact bone. The bone plate may comprise a base portion that comprises a body and an extended portion. The bone plate further may comprise an opening in the base portion that extends from an upper surface of the bone plate to the lower surface of the base plate. The bone plate further may comprise an angled portion located on an opposite end of the base portion from the extended portion. The angled portion may be at an angle with respect to the base portion.

The features and advantages of the present invention will be readily apparent to those skilled in the art. While numerous changes may be made by those skilled in the art, such changes are within the spirit of the invention.

BRIEF DESCRIPTION OF THE DRAWINGS

FIG. 1 is a front view of one embodiment of a bone plate of the present invention.

FIG. 2 is a lateral view of the embodiment of the bone plate of FIG. 1.

FIG. 3 is a front view of another embodiment of a bone plate of the present invention.

FIG. 4 is a lateral view of the embodiment of the bone plate of FIG. 3.

DETAILED DESCRIPTION OF THE INVENTION

Figure 5:
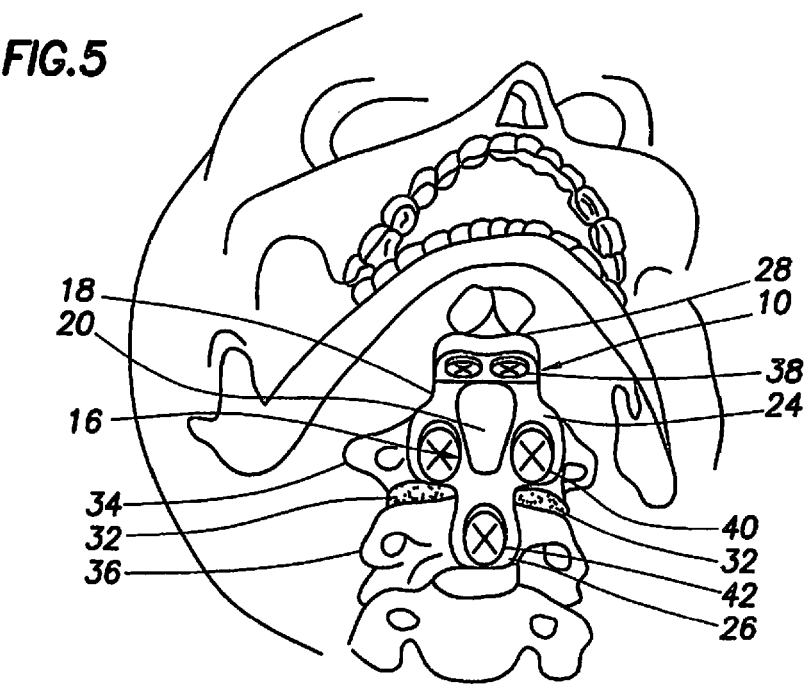
FIG. 5 is an isometric view of one embodiment of a bone plate of the present invention installed in a patient.

The present disclosure generally relates to a fixation device for positioning and immobilizing at least two adjacent vertebra. In particular, in one or more embodiments, the present disclosure relates to an anterior clivus plate that immobilizes at least two adjacent vertebrae.

FIGS. 1-2 illustrate a bone plate 10 in accordance with embodiments of the present invention. The bone plate 10 may be used, for example, in an anterior approach to realign and immobilize the clivus-C1-C2 for a rheumatoid arthritis patient with basilar invagination. Realignment and immobilization of the clivus-C1-C2 may be desirable, for example, for a rheumatoid arthritis patient with basilar invagination of the C2 ondontoid into the foramen magnum of the occiput. As will be appreciated by those of ordinary skill in the art, with the benefit of this disclosure, the bone plate 10 may be a standalone device or may be used in conjunction with one or more additional devices and/or techniques. By way of example, the bone plate 10 may be used in combination with other decompression techniques, such as removal of the anterior C1 arch and/or C2 odontoid.

As illustrated in FIGS. 1-2, the bone plate 10 may include an upper surface 12 and a lower surface 14, with the lower surface 14 configured to contact the bone. The bone plate 10 also may include a base portion 16 and an angled portion 18. The bone plate 10 further may include at least one opening 20 formed in the base portion 16 that extends from the upper surface 12 to the lower surface 14. The bone plate 10 further may include a number of holes 22 configured and adapted to receive fasteners, such as, for example, screws that will affix the bone plate 10 to the bone.

As illustrated in FIGS. 1-2, the base portion 16 may include body 24 and extended portion 26 having a width narrower than the width of the body 24. The width of the extended portion 26 may be, for example, sufficient to accommodate at least one screw, while the width of the base portion 16 may be, for example, sufficient to accommodate at least two screws. The base portion 16 may be configured, for example, to attach to two vertebrae in the cervical region of the spine. For example, the base portion 16 may be configured to attach to the C1 and C2 vertebrae with the body 24 disposed over the C1 vertebrae and the extended portion 26 disposed over the C2 vertebrae.

The base portion 16 further may include at least one opening 20 formed in the base portion 16 that extends from the upper surface 12 to the lower surface 14 of the bone plate 10. The surface area of the opening 20 relative to the surface area of the body 24 of the base portion 16 may be, for example, from about 25% to about 75%. The opening 20 may or may not be centered in the body 24. In addition, the opening 20 may be symmetrical or asymmetrical. The opening 20 may be formed in the base portion 16 to allow access, for example, to the space between adjacent bones. By way of example, the opening 20 may be formed in the base portion 16 to allow access to the space between the C1 and C2 vertebrae. By way of example, fusion of the C1 and C2 vertebrae may be observed by way of the opening 20. In certain embodiments, graft materials and/or synthetic proteins may be placed through the opening 20 to accelerate bone growth between adjacent bones, such as between the clivus and the C1 vertebrae. While the opening 20 is illustrated as generally oval, a wide variety of other shapes may be suitable for the particular purpose, including, for example, circular, oblong, rectangular, square, and the like.

The angled portion 18 may be located on the opposite end of the base portion 16 from the extended portion 26. In general, the angled portion 18 may be at an angle with respect to base portion 16, for example, to allow alignment of the angled portion 18 with the clivus 28 and alignment of the base portion 16 with vertebrae in the cervical region of the spine. As illustrated in FIGS. 1-2, the angled portion 18 may be at an angle of about 90° with respect to the base portion 18. However, other angles may also be suitable in embodiments of the present invention. By way of example, the angle of the angled portion 18 with respect to the base portion 16 may be in the range of from about 90° to about 145°. As further illustrated in FIGS. 1-2, the base portion 16 and the angled portion 18 may be rigidly connected. For example, the base portion 16 and the angled portion 18 may be formed as unitary body. In other embodiments, the base portion 16 and the angled portion 18 may be not be formed as a unitary body.

Holes 22 may be formed in the bone plate 10 that extend from the upper surface 12 to the lower surface 14. In general, the holes 22 may be configured and adapted to receive fasteners, such as, for example, screws that will affix the bone plate 10 to the bone. As illustrated in FIGS. 1-2, two or more of the holes 22 may be formed in the angled portion 18 of the bone plate 10. By way of example, the two or more holes 22 formed in the angled portion 18 may be configured and adapted for alignment with the clivus. In addition, two or more of the holes 22 may be formed in the body 24 of the base portion 16 and at least one of the holes 22 may be formed in the extended portion 26 of the base portion 16. By way of example, the two or more of holes 22 formed in the body 24 may be configured and adapted for alignment with the C1 vertebra, and the hole(s) formed in the extended portion 26 may be configured and adapted or alignment with the C2 vertebra. In certain embodiments, the holes 22 formed in the base portion 16 may be configured and adapted at the C1-C2 transarticular trajectory starting from the lateral mass of the C2 vertebra to the C1 vertebra. While not illustrated, an additional hole may be formed in the bottom edge of the extended portion 26. By way of example, this additional hole could be configured and adapted in the direction of the odontoid from the bottom edge of the extended portion 26.

The screws that may be used to connect the bone plate 10 to the bone may be provided with a spherical head that is selectively engageable with the spherical curvature of the hole, in certain embodiments. An elongate shaft may be connected to the spherical head to allow it to penetrate the bone. Preferably, the elongate shaft may include threads that aid in fixing the bone plate 10 to the bone. It is also preferable to have a hexagonal projection to aid in gripping the screw. The length of the elongate shaft may be varied as desired. The elongate shaft of the screws for use in the holes 22 in the angled portion 18 may have a length, for example, within a range of about 4 millimeters to about 26 millimeters. In one embodiment, the elongate shaft of these screws may have a length of about 20 millimeters. The elongate shaft of the screws for use in the holes 22 in the base portion 16 may have a length, for example, within a range of about 40 millimeters to about 65 millimeters. However, it should be understood that lengths outside the examples disclosed herein are encompassed by embodiments of the present invention.

Embodiments of the bone plate 10 also may include at least one tool engagement feature on the sides and/or top of the plate. While not illustrated, the sides of the bone plate 10 may include, for example, depressions positioned for engaging with an instrument. By way of example, the engaging instrument may contact the bone plate 10 in the depressions thereby enabling the surgeon or user to control the bone plate 10 so that it may be placed in the proper position in the boney elements of the spine. The shape of the depressions should generally allow for the ability to have the screws positioned through a fixed or variable angle connection.

The size of the bone plate 10 may be of any appropriate size required to perform its function. By way of example, the bone plate 10 may be of sufficient length to extend across the clivus, C1 vertebra, and C2 vertebra. In certain embodiments, the length of the bone plate 10 may be within a range of about 26 millimeters to about 69 millimeters. The extended portion 26 may extend, for example, for a length of about 10 millimeters to about 26 millimeters beyond an end of the body 24 that is opposite the angled portion 19. The width of the bone plate 10 may be, for example, within a range of about 30 millimeters to about 60 millimeters. The width of the angled portion 18 of the bone plate 10 may be, for example, within a range of about 10 millimeters to about 30 millimeters. The width of the body 24 of the base portion 16 of the bone plate 10 may be, for example, within a range of about 30 millimeters to about 60 millimeters. The width of the extended portion 26 of the base portion 16 may be, for example, within a range of about 10 millimeters to about 20 millimeters. However, it should be understood that lengths and widths outside the example ranges disclosed herein are encompassed by embodiments of the present invention.

The bone plate 10 may comprise, for example, any of a variety of biocompatible materials, including metals, ceramic materials, and polymers. Examples of biocompatible materials include titanium, aluminum, cobalt-chromium, alloys, and polyethylene. Moreover, the lower surface 14 of the bone plate 10 may include, for example, a plurality of teeth or a porous or macrotexture surface to assist in attaching the bone plate 10 to the bone.

Referring now to FIGS. 3-4, another embodiment of the base plate 10 is illustrated in accordance with embodiments of the present invention. As illustrated in FIGS. 3-4, the angled portion 18 may be pivotably connected to the base portion 16 in certain embodiments of the present invention. In the illustrated embodiment, the base plate 10 further may include a hinge 30 connecting the base portion 16 and the angled portion 18. It should be understood that the pivoted connection (e.g., hinge 30) between the angled portion 18 and the base portion 16 generally should allow for a variety of different angles of the angled portion 18 with respect to the base portion. By way of example, the angle of the angled portion 18 with respect to the base portion 16 may be in the range of from about 90° to about 145°. Moreover, the pivoted connection between the angled portion 18 and the base portion 16, in certain embodiments, generally may be lockable at a predetermined angle when implanted in a patient. For example, it may be desired to lock the angled portion 16 at angle of 90° when the base plate 10 is installed in a patient.

Figure 6:
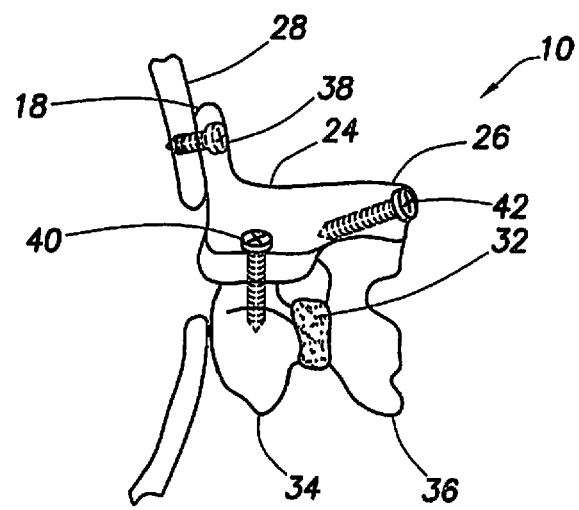
FIG. 6 is a lateral view of one embodiment of a bone plate of the present invention installed in a patient.

FIGS. 5-6 illustrate positioning of the bone plate 10 in a patient in accordance with one embodiment of the present invention. In the illustrated embodiment, a pair of vertebrae spacers 32 is shown between the C1 vertebra 34 and the C2 vertebrae 36. The vertebrae spacers 32 will be described in more detail below with respect to the embodiment of FIG. 7.

As illustrated in FIGS. 5-6, the bone plate 10 may be attached to the clivus 28, the C1 vertebra 34, and the C2 vertebrae 36. The plate may be introduced superiorly at a latero-medial side of a mandible. Partial mandible removal may be required prior to positioning of the plate. In addition, a soft retractor blade may be used for retraction of the trachea and larynx. In the illustrated embodiment, the bone plate 10 may be positioned over the clivus 28, the C1 vertebra 34, and the C2 vertebra 36 with the opening 20 being positioned so that the disc space between the clivus 28 and the C1 vertebra 34 is accessible through the opening 20. In the pivotably connected embodiments, the angled portion 18 may be locked at the desired angled, for example. Clivus screws 38 may be screwed into the clivus through the holes 22 in the angled portion 18 of the bone plate 10. C1 screws 40 may be screwed into the C1 vertebra 34 through the holes in body 24 of the base portion 16 of the bone plate 10. C2 screws 42 may be screwed in the C2 vertebra 36 through the holes in the extended portion 26 of the base portion 16 of the bone plate 10. The bone plate 10 may be attached to the clivus 28, C1 vertebra 34, and C2 vertebra 36 in any suitable order. By way of example, in certain embodiments, the angled portion 18 of the bone plate may be attached to the clivus 28 prior to attachment of the base portion 16 to the C1 vertebra 34 and the C2 vertebra 36. In other embodiments, the base portion 16 of the bone plate 10 may be attached to the C1 vertebra 34 and the C2 vertebra 36 prior to attachment of the angled portion 18 to the clivus 28.

Figure 7:
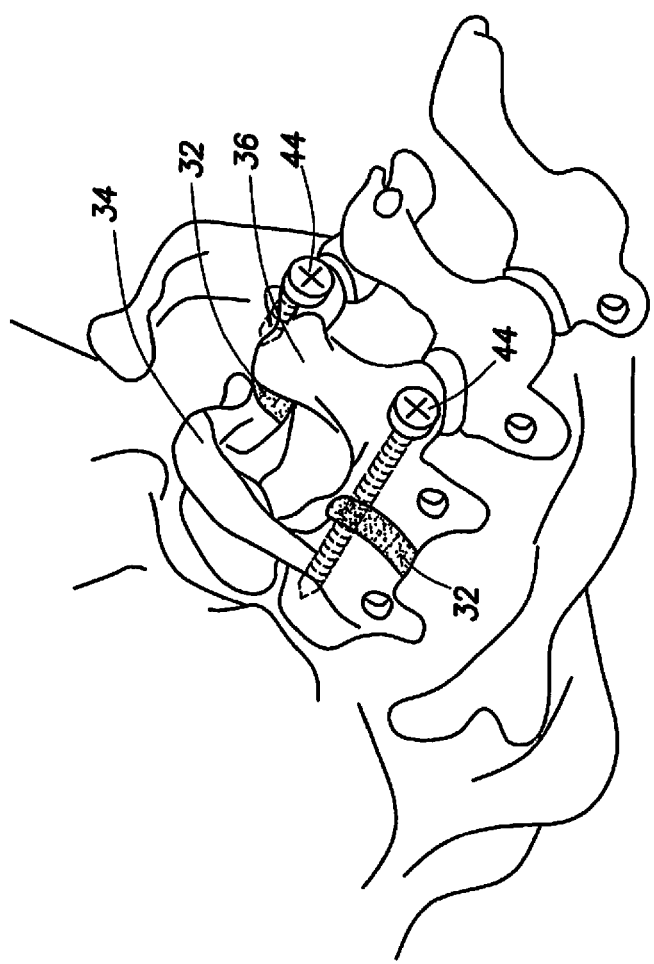
FIG. 7 is a perspective view one embodiment of a spacer of the present invention installed in a patient.

FIG. 7 illustrates a vertebrae spacer 32 in accordance with embodiments of the present invention. The vertebrae spacer 32 may be used, for example, in a posterior approach to restore space between the C1 vertebra 34 and the C2 vertebra 36. Use of the vertebrae spacer 32, for example, to realign and fuse the C1-C2 vertebrae may be desirable for a rheumatoid arthritis patient with basilar invagination of the C2 ondontoid into the foramen magnum of the occiput.

As illustrated in FIG. 7, a pair of vertebrae spacers 32 may be disposed between the C1 and C2 vertebrae. In the illustrated embodiment, the vertebrae spacers 32 are shaped to fit between the superior and inferior lateral masses of the cervical spine. In another embodiment, the vertebrae spacers 32 may be u-shaped, thereby allowing for a lateral approach to restoring space between the C1 vertebra 34 and the C2 vertebra 36. In addition, each of the vertebrae spacers 32 may include one or more holes that are configured and adapted to receive fasteners, such as, for example, screws 44 that will affix the spacers 32 to the bone. The screws 32 may be a fully or partially threaded long screw. In other embodiments, the vertebrae spacers 32 may not include a hole for the fastener, but instead, the vertebrae spacers 32 may be made from a material into which a fastener can be drilled without any pre-defined trajectory. By way of example, vertebrae spacers 32 may be made from a polymeric material similar to MicroFuse™ granules, which are available from Globus Medical, Inc.

While the vertebrae spacers 32 are illustrated in FIG. 7 as a standalone device, the vertebrae spacers 32 may also be used in combination with one or more additional devices and/or techniques. By way of example, the vertebrae spacers 32 may be used in combination with an anterior plate that bridges the C1 and C2 vertebrae, such the bone plate 10. By way of further example, the vertebrae spacers 32 may be used in combination with wiring of the C1 and C2 vertebrae with a bone graft. By way of further example, the vertebrae spacers 32 may be used in combination with a post rod and wiring of the C1 and C2 vertebrae. By way of further example, the vertebrae spacers 32 may be used in combination with a cable through the occiput. In yet another embodiment, a screw may be used to secure the C1 vertebra and the occiput.

The vertebrae spacers 32 may comprise, for example, any of a variety of biocompatible materials, including metals, ceramic materials, and polymers. Examples of biocompatible materials include titanium, stainless steel, aluminum, cobalt-chromium, alloys, and polyethylene. Moreover, surfaces of the vertebrae spacers 32 may include, for example, a plurality of teeth or a porous or macrotexture surface to assist in attaching the vertebrae spacer to the bone.

While it is apparent that the invention disclosed herein is well calculated to fulfill the objects stated above, it will be appreciated that numerous modifications and embodiments may be devised by those skilled in the art.

What is claimed is:

1. An implantable device comprising a bone plate having a lower surface configured to contact bone, wherein the bone plate comprises:
   a base portion comprising a body and having at least one hole for receiving a screw;
   a singular opening in the base portion that extends from an upper surface of the bone plate to the lower surface of the base portion, wherein the singular opening has an area that is about 25% to about 75% of a total area of an anterior-facing surface of the body; and
   an angled portion located on an end of the base portion, wherein the angled portion is at an angle with respect to the base portion, wherein the angled portion is configured to attach to a patient's clivus while a vertebral spacer separate from the angled portion is positioned between the patient's C1 and C2 vertebrae,
   wherein the at least one hole of the base portion extends from the upper surface of the bone plate to the lower surface of the bone plate and wherein the at least one hole is angled such that opening of the hole at the upper surface of the plate is further away from the angled portion than the opening of the hole at the lower surface of the plate.

2. The implantable device of claim 1, wherein the bone plate has a length of about 26 millimeters to about 69 millimeters.

3. The implantable device of claim 1, wherein the angled portion is at an angle of from about 90° to about 145° with respect to the base portion.

4. The implantable device of claim 1, further comprising an extended portion, the extended portion extending from an opposite end of the base portion than the angled portion.

5. The implantable device of claim 4, wherein the base portion is configured for attachment to a patient's C1 and C2 vertebrae with the body disposed over the C1 vertebra and the extended portion disposed over the C2 vertebra.

6. The implantable device of claim 5, wherein the singular opening is configured to allow access to space between the C1 vertebra and C2 vertebra.

7. The implantable device of claim 4, wherein the extended portion extends for a length of about 10 millimeters to about 26 millimeters beyond an end of the body that is opposite the angled portion, and wherein the extended portion has a width of about 10 millimeters to about 20 millimeters.

8. The implantable device of claim 4, wherein the extended portion includes at least one hole for receiving a bone screw and wherein the angled portion includes at least one hole for receiving a bone screw.

9. The implantable device of claim 1, wherein the angled portion and the base portion are unitary.

10. The implantable device of claim 1, wherein the angled portion and the base portion are pivotably connected.

11. The implantable device of claim 10, wherein the angled portion pivots at an angle of from about 90° to about 145° with respect to the base portion.

12. The implantable device of claim 10, wherein the angled portion is configured for locking at a predetermined angle with respect to the base portion.

13. The implantable device of claim 1, wherein the base portion further comprises a hinge connecting the base portion and the angled portion.

14. A bone fixation system comprising:
 a bone plate having a lower surface configured to contact bone, wherein the bone plate comprises:
  a base portion comprising a body and an extended portion;
  a singular opening in the base portion that extends from an upper surface of the bone plate to the lower surface of the base portion, wherein the singular opening has an area that is about 25% to about 75% of a total area of an anterior-facing surface of the body;
  an angled portion located on an opposite end of the base portion from the extended portion, wherein the angled portion is at an angle with respect to the base portion,
  wherein the base portion is configured for attachment to a patient's C1 and C2 vertebrae with the body disposed over the C1 vertebra and the extended portion disposed over the C2 vertebra, wherein the angled portion is configured for attachment to the patient's clivus, and
  wherein the singular opening is configured to allow access to space between the patient's clivus and C1 vertebra,
  wherein the base portion further comprises a hinge connecting the base portion and the angled portion for angular adjustment; and
 a vertebrae spacer, formed separate from the angled portion, configured for positioning between the patient's C1 and C2 vertebrae, wherein the vertebrae spacer comprises a hole for receiving a screw for affixing the vertebrae spacer to bone, and spacer screws for affixing the vertebra spacer to bone.

15. The implantable device of claim 14, wherein the angled portion is pivotable at an angle of from about 90° to about 145° with respect to the base portion.

16. The implantable device of claim 14, wherein the extended portion extends for a length of about 10 millimeters to about 26 millimeters beyond an end of the body that is opposite the angled portion, and wherein the extended portion has a width of about 10 millimeters to about 20 millimeters.

17. The implantable device of claim 14, wherein the base portion has at least one hole for receiving a screw.

18. The implantable device of claim 17, wherein the at least one hole extends from the upper surface of the bone plate to the lower surface of the bone plate and wherein the at least one hole is angled such that opening of the hole at the upper surface of the plate is further away from the angled portion than the opening of the hole at the lower surface of the plate.

\* \* \* \* \*